US011345892B2

(12) United States Patent
Larsen

(10) Patent No.: US 11,345,892 B2
(45) Date of Patent: May 31, 2022

(54) CENTRIFUGAL SYRINGE AND METHOD FOR BLOOD FRACTIONATION

(71) Applicant: Herbert A F Larsen, Abbotsford (CA)

(72) Inventor: Herbert A F Larsen, Abbotsford (CA)

(*) Notice: Subject to any disclaimer, the term of this patent is extended or adjusted under 35 U.S.C. 154(b) by 0 days.

(21) Appl. No.: 15/598,757

(22) Filed: May 18, 2017

(65) Prior Publication Data
US 2018/0333530 A1 Nov. 22, 2018

(51) Int. Cl.
B01L 3/00 (2006.01)
C12N 5/078 (2010.01)
A61M 1/02 (2006.01)
A61B 5/15 (2006.01)
B01L 3/02 (2006.01)
A61B 5/153 (2006.01)
A61M 5/315 (2006.01)

(52) U.S. Cl.
CPC ............ C12N 5/0644 (2013.01); A61B 5/153 (2013.01); A61B 5/15003 (2013.01); A61B 5/150236 (2013.01); A61B 5/150244 (2013.01); A61M 1/029 (2013.01); A61M 1/0272 (2013.01); B01L 3/0217 (2013.01); B01L 3/5021 (2013.01); A61M 5/31511 (2013.01); A61M 2202/0427 (2013.01); A61M 2202/0429 (2013.01); B01L 2200/026 (2013.01); B01L 2200/0605 (2013.01); B01L 2200/0652 (2013.01); B01L 2200/0689 (2013.01); B01L 2300/0832 (2013.01); B01L 2400/0478 (2013.01)

(58) Field of Classification Search
CPC .......... B01L 3/0217; B01L 2400/0409; B01L 2300/041

USPC ................................ 422/527, 546, 533, 548
See application file for complete search history.

(56) References Cited

U.S. PATENT DOCUMENTS

| 3,965,889 A | 6/1976 | Sachs |
| 4,020,831 A | 5/1977 | Adler |
| 4,459,997 A | 7/1984 | Sarstedt |
| 4,492,634 A | 1/1985 | Villa-Real |
| 5,577,513 A | 11/1996 | Van Vlasselaer |
| 5,704,918 A * | 1/1998 | Higashikawa .......... A61M 5/19 604/191 |

(Continued)

FOREIGN PATENT DOCUMENTS

EP 0209976 A1 1/1987

Primary Examiner — Natalia Levkovich

(57) ABSTRACT

Disclosed is a centrifugable syringe and syringe components for use in blood fractionation. Also disclosed is a method of blood fractionation using the syringe. The syringe comprises a substantially transparent barrel, a substantially transparent, elongated delineation neck, a plunger for drawing blood into and expelling blood from the barrel, and an adapter attached to the neck for enabling releasable connection of a selected device over an inlet/outlet opening in the neck. The delineation neck extends away from a distal end of the barrel. The barrel and the neck have respective axial bores in fluid flow communication with each other, the cross sectional area of the bore in the delineation neck being substantially less than the cross sectional area of the bore in the barrel. The selected device may be one of various devices including a capping device sealing the inlet/outlet opening of the neck, a needle device used during withdrawal of blood from a subject through the neck, or a hose device used to carry away delineated blood fractions from the syringe through the neck.

8 Claims, 7 Drawing Sheets

(56) References Cited

U.S. PATENT DOCUMENTS

| | | | |
|---|---|---|---|
| 6,682,243 B2 | 1/2004 | Iwamoto et al. | |
| 6,716,187 B1 | 4/2004 | Jorgensen et al. | |
| 7,195,606 B2 | 3/2007 | Ballin | |
| 7,452,344 B2 | 11/2008 | Jorgensen et al. | |
| 7,976,796 B1 | 7/2011 | Smith et al. | |
| 8,567,609 B2 | 10/2013 | Landrigan et al. | |
| 8,709,796 B2 | 4/2014 | Faure et al. | |
| 8,992,482 B2 | 3/2015 | Fojtik | |
| 9,050,403 B2 | 6/2015 | Morimoto et al. | |
| 9,239,276 B2 | 1/2016 | Landrigan et al. | |
| 2004/0256331 A1 | 12/2004 | Arking et al. | |
| 2010/0025342 A1* | 2/2010 | Morimoto | A61B 5/1416 210/787 |
| 2014/0371048 A1 | 12/2014 | Ra et al. | |

\* cited by examiner

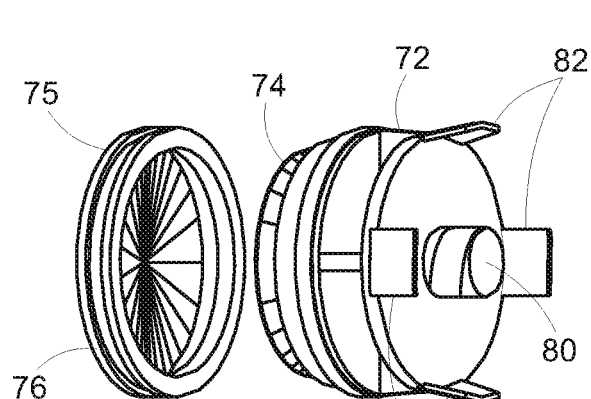
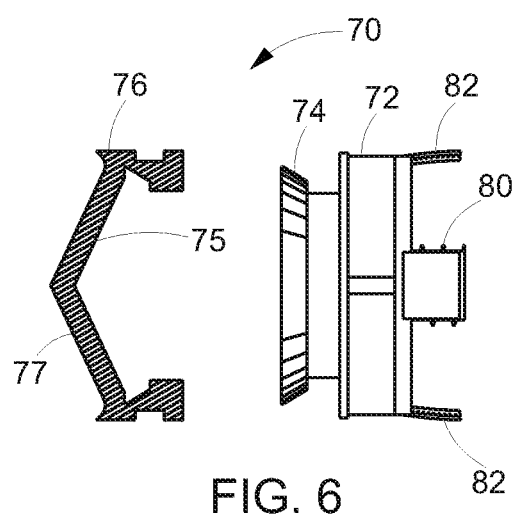
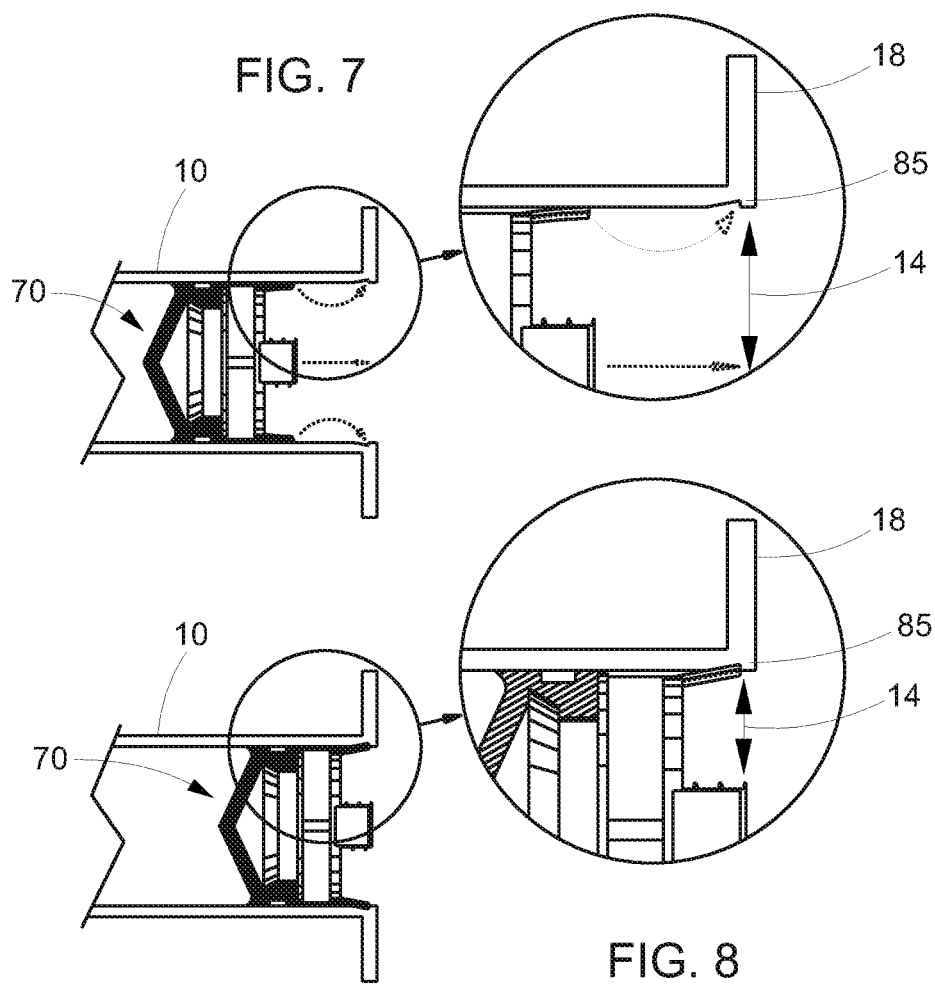

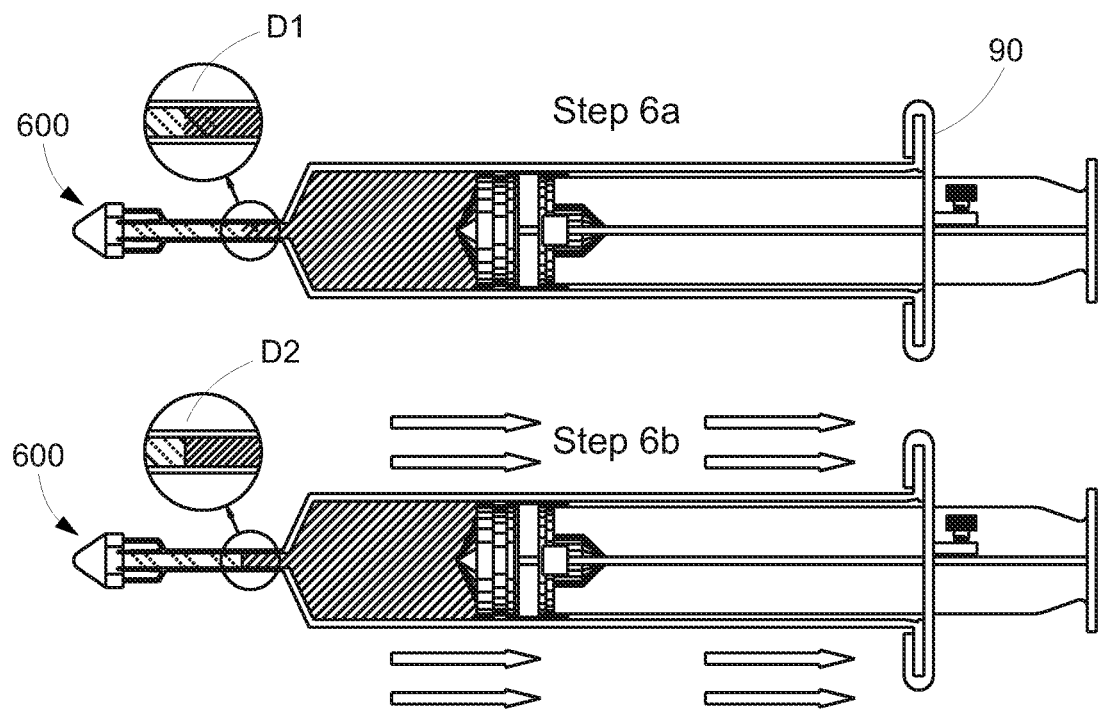
FIG. 10
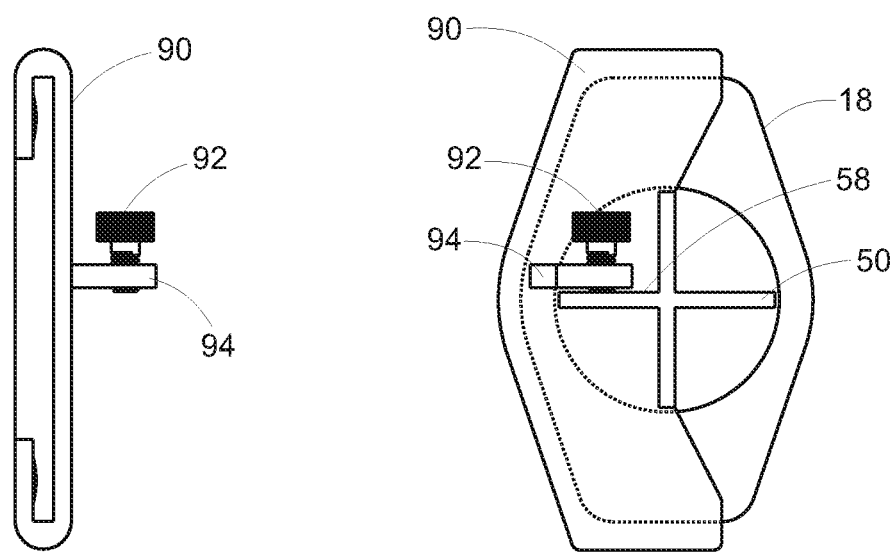
FIG. 11
FIG. 12

CENTRIFUGAL SYRINGE AND METHOD FOR BLOOD FRACTIONATION

CROSS-REFERENCE TO RELATED APPLICATIONS

This application is related to U.S. provisional application No. 62/338,450 filed May 18, 2016, entitled "PLATELET RICH PLASMA BLOOD FRACTIONATION SYRINGE", naming Herbert A. F. Larsen as the inventor. The contents of the provisional application are incorporated herein by reference in their entirety, and the benefit of the filing date of the provisional application is hereby claimed for all purposes that are legally served by such claim for the benefit of the filing date.

BACKGROUND OF THE INVENTION

This invention relates to blood fractionation, devices used for blood fractionation and components of such devices.

Blood platelets contain various growth factors and other cytokines that are known to stimulate the healing of both bone and soft tissue. Accordingly, there is an inherent need for a device that allows for the concentration of such platelets in a blood fraction as well as the ability to remove and separate various blood fractions without cross contaminating a selected fraction with an immediate adjacent fraction.

Since the Platelet Rich Plasma (PRP) process leading to a concentrated source of generally autologous, platelets requires the fractionation of blood into basically three broad fractions: the most dense fraction of the whole blood being erythrocytes (red blood cells) at a volume of roughly 45%; the second most dense fraction being the buffy coat (leukocytes and platelets) at a volume of less than 1%; and the lightest density fraction being plasma at a volume of 55%, the use of a centrifuge is a preferred method of fractionation. The resulting fractions are shown in FIG. 15 which illustrates a column of blood together with an arrow indicating the direction of centrifugal force.

Once the whole blood is centrifuged into its component fractions, the most critical issue then becomes: how does one classify, or otherwise separate, fraction from an adjacent fraction? As persons skilled in the art will be aware, the sought after fraction in the PRP process (e.g. the platelets fraction shown in FIG. 15) is typically comprised of less than 1% of the entire volume of whole blood. To loose some of that fraction to, or to have that fraction gain volume from, either the erythrocytes fraction shown in FIG. 15 or the plasma fraction shown in FIG. 15 through comingling, is to defeat the process of removing the highest level of platelet concentration available.

Traditionally, when the need arises to extract and separate blood into component parts, such as the segregation of plasma, platelets and erythrocytes, the blood is drawn from an individual into a blood bag which is then centrifuged to stratify the blood into differing fractions based on their bulk densities. From this point, the fractions are either extracted by inserting an object, such as a needle, into the blood bag whereby the fractions then can be withdrawn one at a time or the bag is gently compressed to force the blood out of an exit point in the bag with the extraction process stopped at the best achievable point between each transition from one fraction to another.

Two major problems exist with the foregoing methodology.

1. Since the bag possesses pliable walls, and since the line of delineation between the blood fractions upon centrifuge completion should remain sharp, any movement between the fractions or distortion in the bag wall may cause the points of delineation between fractions to blend and become comingled. When comingling takes place, the need for accurate segregations, as is required when raw platelets are sought, is lost to mechanical disruption. Then, an attempt to segregate can often prove futile.

2. At any point of component blood transfer, whereby either an object is inserted into a holding chamber for the purpose of extraction or an object is fixed to the outlet of the chamber, there exists the possibility of introducing a contaminant or pathogen into the blood reserve. For obvious reasons, blood that has been tainted with an external contaminant may have adverse consequences. Therefore, much effort has been engaged in by medical science to both increase the quality and delineation of segregated blood fractions while at the same time maintaining sterile controls.

In response to the problem of flexible containment as found with blood bags, a number of patents exist wherein a rigid wall containment is used for centrifuging the blood fractionations. One of the more effective solutions to the comingling problem which occurs with blood segregations in a flexible walled containment is to carry out the centrifuge and extraction process within a rigid-walled chamber. The idea is that when blood is moved in a linear fashion in a containment with fixed and rigid sides then there will be considerably less turbulence taking place between blood fractionations. Patent documents such as U.S. Pat. Appln. Pub. No. 2014/0054246 (Fojtik); U.S. Pat. Appln. Pub. No. 2010/0025342—now U.S. Pat. No. 9,050,403 (Morimoto et al.); U.S. Pat. Appln. Pub. No. 2005/0261620—now U.S. Pat. No. 7,195,606 (Ballin); U.S. Pat. Appln. Pub. No. 2004/0256331 (Arking et al.); U.S. Pat. Appln. Pub. No. 2004/0167004—now U.S. Pat. No. 7,452,344 (Jorgensen et al.); U.S. Pat. No. 7,976,796 (Smith et al.); U.S. Pat. No. 6,716,187 (also Jorgensen et al.); U.S. Pat. No. 5,577,513 (Van Vlasselaer); U.S. Pat. No. 4,492,634 (Villa-Real); U.S. Pat. No. 4,459,997 (Sarstedt); U.S. Pat. No. 4,020,831 (Adler); and U.S. Pat. No. 3,965,889 (Sachs), disclose the use of rigid wall containment. From the point of view of flexible verses rigid wall containment, these patent documents offer an improved option.

However, other limitations can be found in the prior art. For example, when blood fractions are evacuated, discharged, or otherwise removed from a blood chamber, one of two problems can arise. First, an inherent deficiency exists because the cross sectional area of the delineation between blood fractions is relatively large in relation to the length and volume of the chamber in which the fractions have been centrifuged. The larger the cross sectional area between, for example, the erythrocytes fraction and the platelet fraction, the more difficult it is to either draw off or excrete one fraction from the other. In an attempt to reduce the cross sectional area between fractions, U.S. Pat. Appln. Pub. No. 2014/0371048 (Ra et al.) discloses a narrowed hour glass shaped region between the erythrocytes fraction and the platelets fraction. The hour glass shaped region provides a significantly reduced cross sectional area between the two fractions and with a significantly reduced transition in which to segregate the fractions. Ra et al. further disclose a plunger/sealer device in which the blood fractions can be mechanically separated.

Although the approach taken by Ra et al. can be seen as an advancement over the prior art mentioned above (viz. in terms of creating a better delineation between blood fractions), it lacks in two significant areas:

1. it relies on an external extraction process which requires the blood to be injected into a separation chamber from an intermediary device. This extra step creates an added risk of introducing contamination into the blood.

2. it relies on the use of an external device (presumably a needle) to extract each of the blood fractions thus creating further possibilities of contaminating the blood.

Generally, there are two distinct negative issues present in prior art, either:

1. an inability to evacuate, discharge, or otherwise remove one fraction from another with a high degree of accuracy; or, 2. an inherent inability to maintain a low chance of external contaminant introduction through a reduced number of mechanical transitions, such as a plurality of blood chambers, needle exchanges, needle penetrations, etc.

The present invention addresses such issues.

BRIEF SUMMARY OF THE INVENTION

The present invention relates to a multi-purpose syringe which possesses the broad functionality to allow the extraction and containment of blood, the centrifuging of blood into various blood fractions while yet in the syringe, and then, without using external extraction methodologies, the discharge of such blood fractions into finely delineated segregations.

In accordance with the present invention there is provided a centrifugable syringe for use in blood fractionation, the syringe comprising a substantially transparent barrel, a substantially transparent, elongated delineation neck, a plunger for drawing blood into and expelling blood from the barrel, and an adapter attached to the neck for enabling releasable connection of a selected device over an inlet/outlet opening of the neck.

The barrel has an axial bore defined by a bore wall and extends from a mouth opening at a proximal end of the barrel to a distal end opening at a distal end of the barrel. Each of the openings has an associated cross sectional area, the cross sectional area of the distal end opening being substantially less than the cross sectional area of the mouth opening.

The delineation neck [[extends away from the distal end of the barrel]] has a proximal end merging with the distal end of the barrel and extends away therefrom to a distal end of the neck and has an axial bore in fluid flow communication with the axial bore of the barrel. The axial bore of the neck extends lengthwise through the neck to the aforementioned inlet/outlet opening and has an opening area substantially the same as the opening area of the distal end opening of the barrel.

The plunger comprises a fluid sealing member for slidably bearing against the bore wall of the barrel to prevent the flow of blood from the barrel through the barrel mouth and is advanceable and retractable within the axial bore of the barrel. It further comprises a handle releasably connect to the sealing member for enabling the advancement and retraction of the sealing member within the axial bore of the barrel. Preferably, the handle is releasably attachable to the syringe barrel.

The delineation neck may be formed integrally with the syringe barrel, or be releasably attachable to the syringe barrel, and is an important feature of the present invention. Since the axial bore of the neck has a cross sectional area substantially less than that of the syringe barrel, a much finer delineation can be made between any two blood fractions within the neck as centrifuged blood is slowly discharged from the syringe through the inlet/outlet opening in the neck.

The selected device which is connectable over the inlet/outlet opening of the delineation neck may be one of various devices, including:

a capping device releasably engageable with the aforementioned adapter to removably cap and seal the inlet/outlet opening in the neck. Such a device would be used to contain blood within the syringe during centrifuge operations;

a needle device releasably engageable with the aforementioned adapter to enable the withdrawal of blood from a subject into the syringe;

a hose device releasably engageable with the aforementioned adapter to carry away blood expelled from the syringe.

The adapter and the selected device which is releasably engageable with the adapter obviously require cooperating parts to enable suitable engagement. Those skilled in art will recognize that cooperative male and female luer fittings may be ideal for this purpose. However, they will also recognize that suitable engagement may be achieved by other (possibly less desirable) means.

Preferably, the fluid sealing member comprises a framework, a flexible seal supported by the framework for slidably bearing against the bore wall of the syringe barrel, and an adapter supported by the framework for enabling releasable connection of the plunger handle to the member.

Advantageously, the flexible seal comprises a flexible side wall for bearing against the bore wall and a flexible conical face projecting from the side wall forward of the framework. The conical face serves to translate axial forces applied to the face to a lateral outward force on the bore wall.

To further advantage, the fluid sealing member further comprises a plurality of flexible locking tabs peripherally supported by the framework, the tabs for slidably bearing outwardly from the framework against the bore wall and for engaging a perimetric locking groove in the bore wall to restrain egress of the sealing member through the mouth of the syringe barrel during centrifuge operations.

To still further advantage, the syringe may include a plunger handle lock for engaging both the handle and a flange extending outwardly from the mouth opening of the barrel to hold the fluid sealing member at a selected position within the barrel during centrifuge operations. This is useful when it is desired to position the fluid sealing member at a location within the barrel where the locking tabs are unable to engage the locking groove.

In another aspect of the present invention, there is provided for use in combination with a syringe barrel having an axial bore for holding blood, the bore itself having an associated cross sectional area measured transverse to the bore:

a substantially transparent elongated delineation neck having an axial bore extending therethrough for viewing centrifuged blood fractions following the centrifuge of blood while carried within the bore of the barrel and the bore of the neck, the bore of the neck being in fluid flow communication with the bore of the barrel during centrifuge operations and having an associated cross sectional area measured transverse to the bore of the neck which is substantially less than the cross sectional area of the bore of the barrel.

In yet another aspect of the present invention there is provided a method of blood fractionation, comprising:

(a) providing a syringe described above (b) releasably connecting a needle device to the delineation neck of the syringe;

(c) drawing blood from a subject through a needle device and the delineation neck into the syringe;

(d) disconnecting the needle device from the delineation neck;

(e) capping and sealing the inlet/outlet opening in the delineation neck with a removable capping device;

(f) centrifuging the blood within the syringe to separate the blood into delineable blood fractions;

(g) removing the capping device;

(h) expelling one or more delineated blood fractions through the inlet/outlet opening from the syringe.

The foregoing method may further include the step of recentrifuging at least a portion of the blood before all of the blood is expelled from the syringe. Advantageously, this may sharpen the delineation between any two blood fractions.

The foregoing and other features and advantages of the present invention will now be described with reference to the drawings in which:

BRIEF DESCRIPTION OF THE DRAWINGS

FIG. 5 is an enlarged exploded perspective view of the piston assembly which appears in FIGS. 2-4 and which is hidden from view in FIG. 1.

FIG. 6 is an exploded side elevation view of the piston assembly.

FIG. 7 is a cross sectional view, partially cut away, and an accompanying detail view of the piston assembly inside the syringe barrel with locking tabs out of engagement with a locking groove in the syringe barrel.

FIG. 8 shows views similar to FIG. 7 but with the piston assembly moved to a position where the locking tabs are in engagement with the locking groove.

FIG. 10 is a pictorial flow chart of additional steps which may be taken between Steps 6 and 7 shown in FIG. 9 if a finer delineation is desired between any two blood fractions. FIG. 10 also illustrates the inclusion of a plunger handle lock which engages both a flange extending outwardly from the syringe barrel and the plunger handle.

FIG. 11 is an enlarged side elevation view of the plunger handle lock shown in FIG. 10.

FIG. 12 is a top view illustrating engagement between the plunger handle lock and the plunger.

DETAILED DESCRIPTION OF THE INVENTION

Figure 1:
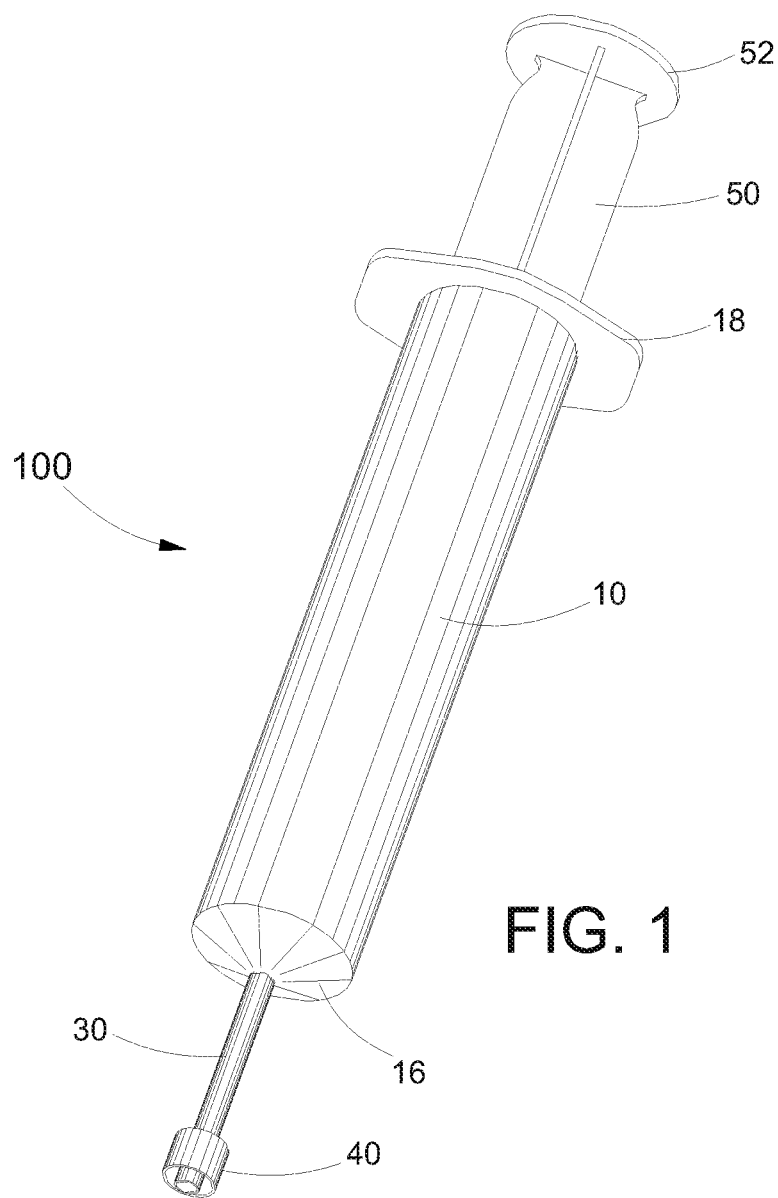
FIG. 1 is a perspective view of a centrifugable syringe in accordance with the present invention.
Figure 2:
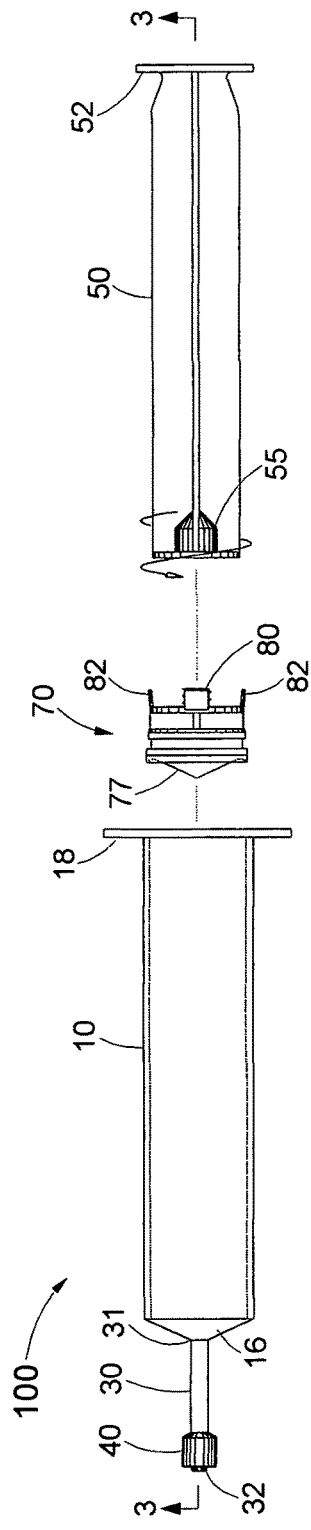
FIG. 2 is a partially exploded side elevation view of the syringe shown in FIG. 1.

Referring now to the drawings, there is shown a centrifugable syringe generally designated 100, the syringe comprising a substantially transparent barrel 10, a substantially transparent, elongated delineation neck 30, an adapter 40 attached to neck 30, and a plunger formed by the combination of a handle 50 and a fluid sealing member or piston assembly generally designated 70.

As depicted, barrel 10 and neck 30 are generally cylindrical. Other components are routinely designed to fit with the cylindrical configuration in a cooperative manner. However, while a cylindrical configuration is preferred, it is not considered essential.

Substantial transparency means transparency which is sufficient to enable blood and any blood fractions which result after the blood is centrifuged to be viewed through the wall of barrel 10 and/or neck 30, as the case may be.

Figure 3:
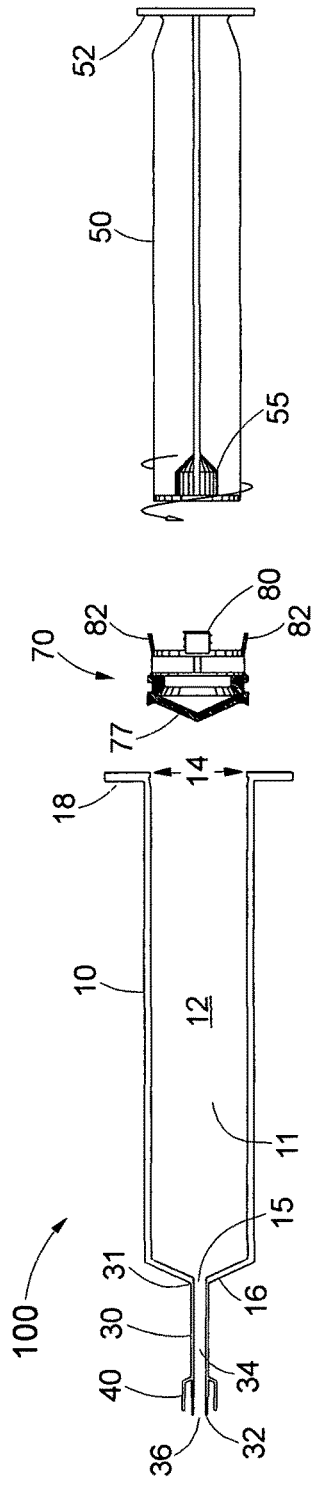
FIG. 3 is a cross sectional view taken along section line 3-3 in FIG. 2.

Barrel 10 has an axial bore 11 defined by bore wall 12 and extends from a mouth opening 14 best seen in FIG. 3 to a distal end opening 15 at distal end 16 of the barrel. Barrel 10 also includes a flange 18 extending outwardly from opening 15. This flange has a conventional shape characteristic of many medical syringes and is designed to be easily gripped with fingers. As best seen in FIGS. 7 and 8, barrel 10 also includes a locking groove 85, the purpose of which is described below in more detail.

Figure 4:
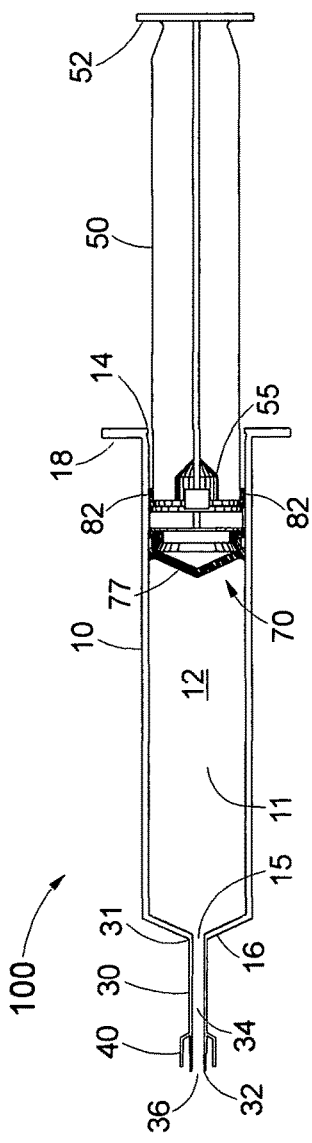
FIG. 4 is a cross sectional view similar to that shown in FIG. 2 but instead showing the components in an engaged position.

As will be apparent from FIGS. 3 and 4, the opening area of distal end opening 15 is substantially less than that of mouth opening 14. In the cylindrical embodiment shown, an example would be where mouth opening 14 has a diameter of about 25 mm. defining an opening area of about 491 $mm^2$, and where distal end opening 15 has a diameter of about 3 mm. defining an opening area of about 7 $mm^2$.

Delineation neck 30 has a proximal end 31 merging with distal end 16 of the barrel and extends away therefrom to its own distal end 32 with an inlet/outlet opening 36. It has an axial bore 34 in fluid flow communication with axial bore 11 of the barrel and extends lengthwise through the neck to inlet/outlet opening 32. As will be apparent from FIGS. 3 and 4, bore 34 has an opening area which is substantially the same as the opening area of distal end opening 15 of the barrel. Neck 30 not only provides a narrowed down opening area compared to that of barrel 10, but also allows viewing of the delineation between blood fractions as blood is being expelled from the syringe through opening 32.

Figure 9:
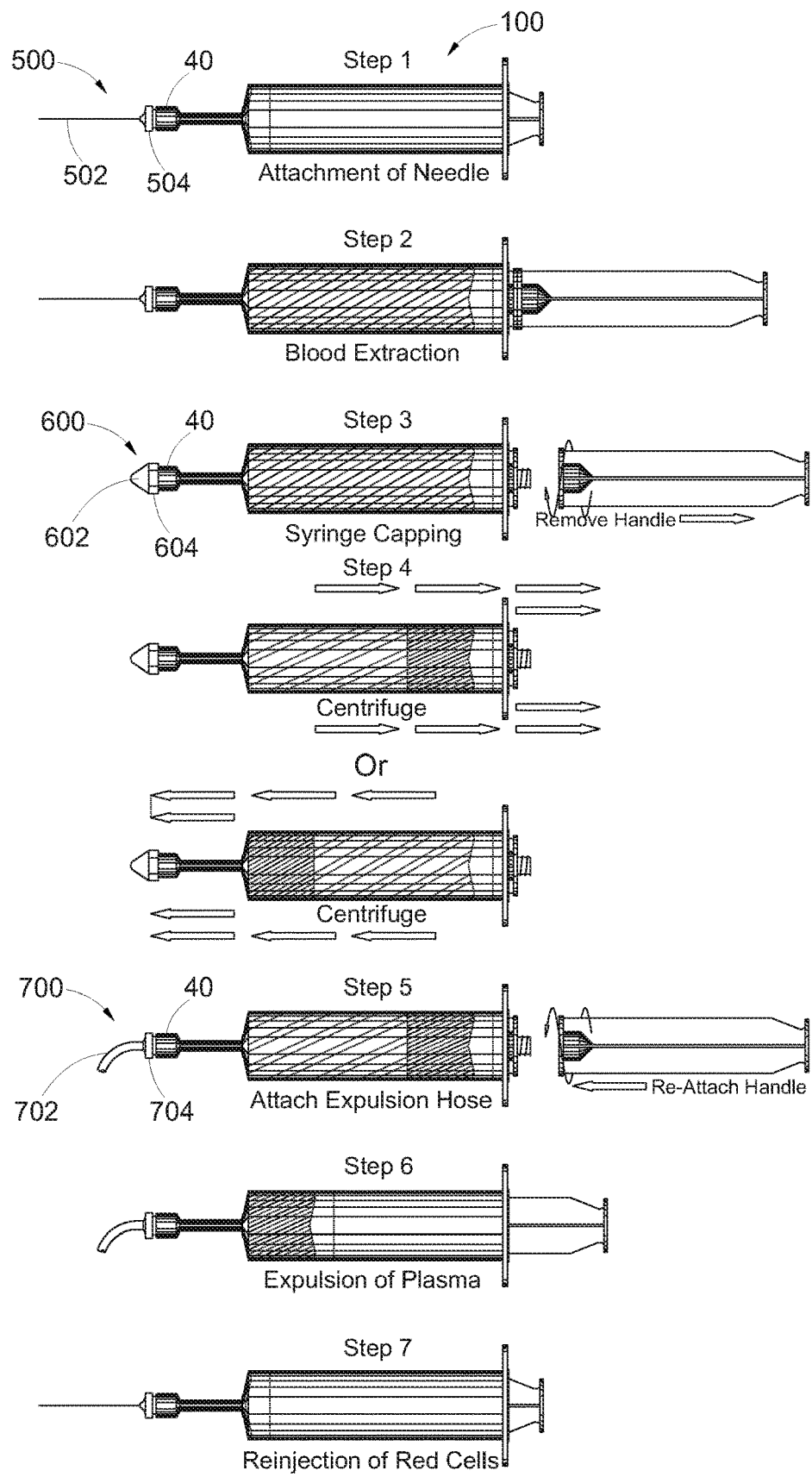
FIG. 9 is a pictorial flow chart of steps made possible by characteristics of the present invention.

Adapter 40 is attached to neck 30 proximate inlet/outlet opening 32, preferably in an integral manner, and enables the releasable connection of a selected device over the opening. The selected device, which should not be considered as part of the present invention, may be one of various devices including:

a needle device generally designated 500 comprising a hypodermic needle 502 and fitting 504 as shown in FIG. 9;

a capping device generally designated 600 comprising a cap 602 and fitting 604 as shown in FIG. 9; or, a hose device generally designated 700 comprising a hose 702 and fitting 704 as shown in FIG. 9.

In the present embodiment, adapter 40 and distal end 32 of the neck together provide a luer male fitting. Fittings 504, 604 and 704 each provide a cooperative luer female fitting.

Such fittings are well known to those skilled in the art and are not described or shown here in any more detail.

Figure 14:
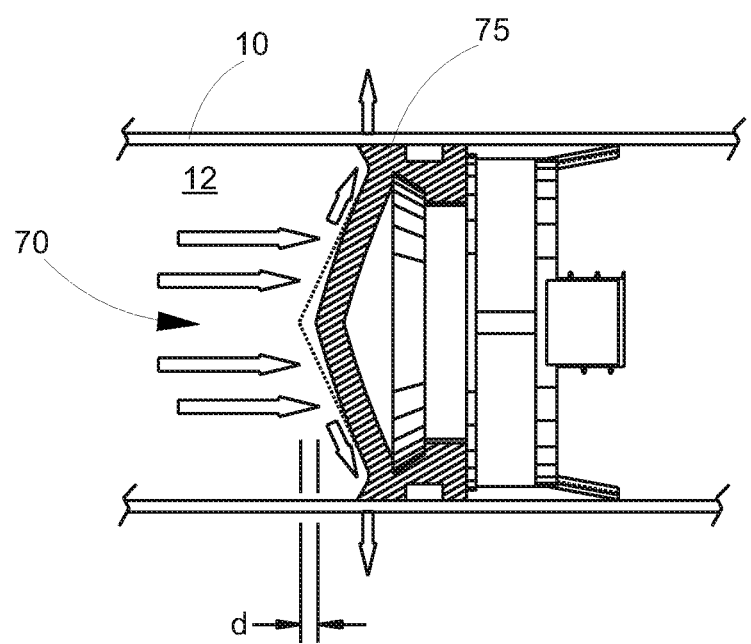
FIG. 14 is a cross sectional view of the piston assembly showing the action and translation of centrifugal forces acting on a flexible seal forming part of the assembly and bearing against the bore wall of the syringe barrel.

Handle 50 extends from a head 52 to an internally threaded connector 55 which is releasably connectable to externally threaded connector 80 forming part of piston assembly 70. As best seen in FIGS. 5 and 6, piston assembly 70 comprises two parts—a flexible rubber seal 75 and a plastic framework 72. The framework is integrally formed and includes a retainer ring 74 which permits snap fitting engagement of the seal with the framework. Connector 80 is integrally formed with the framework. The seal includes a flexible side wall 76 for bearing against bore wall 12 (see FIGS. 3, 4) and a flexible conical face 77 projecting forward of the framework. As indicated by the right facing horizontal arrows and diagonal arrows in FIG. 14, axial forces bearing on the seal are translated by the conical face and side wall to a lateral outward force on the bore wall. As pressure is increased against the face, it detents slightly by a distance "d" which in turn redirects the force down the plane of the face, and inherently produces a lateral outward force against the wall. The net effect is to increase sealing pressure and to produce a stronger seal between the piston assembly and the bore wall.

Piston assembly 70 also includes a plurality (4) of flexible locking tabs 82 which are integrally formed with and thereby supported by the framework. In use the tabs slidably bear outwardly from the framework against bore wall 12 and, as best seen in FIGS. 7 and 8, are designed to engage aforementioned locking groove 85 in the bore wall as the piston assembly reaches mouth opening 14 of barrel 10. Such engagement serves to restrain egress of the piston assembly through the mouth opening during centrifuge operations.

At times, and as is discussed below, it is desirable during centrifuge operations to restrain movement of piston assembly 70 within barrel 10 at a distance away from mouth opening 14.

Referring now to FIG. 9 there are shown several typical steps involved when syringe 100 is being used as an apparatus for blood fractionation.

Step 1 demonstrates the need to attach needle device 500 to adapter 40 of the syringe.

Step 2 demonstrates whole blood within the syringe after extraction from a subject.

Step 3 demonstrates a usual preference or need to remove the needle device and replace it with capping device 600. In addition, it is at this step, preliminary to centrifuge operations, that the plunger handle is unthreaded, or otherwise removed.

Step 4 with arrows indicating alternative directions of centrifuge forces demonstrates the location of syringe 100 in a centrifuge (not shown) where the whole blood is spun into density gradients of blood, primarily three fractions, that of red blood cells, plasma and a buffy coat (leukocytes and platelets). Because of the ability of this invention to stop the piston assembly from exiting the barrel, the blood can be fractionated such that upon centrifuging, the red blood cells can be concentrated at either the end of the barrel or the piston assembly position, depending on the direction of centrifugal force chosen, thus allowing the expulsion of red blood cells either first in the process or last.

Step 5 demonstrates reattachment of the plunger handle in preparation for the process of expelling the blood from syringe 100 through hose device 700. This particular example shows the red blood cells centrifuged towards the piston assembly thus they will be expelled last.

Step 6 demonstrates the first step in the blood expulsion process, that of expelling the plasma and then the leukocytes and platelets. Expulsion of each fraction takes place until such time as the delineation between fractions is visually observed to be present in the delineation neck. Note: If co-mingling between any two fractions has taken place, for example, if the delineation between red blood cells and the buffy coat (leukocytes and platelets) is blurred by the two fractions having blended, the option is available to take additional steps as is discussed below with reference to FIG. 10.

Step 7 demonstrates the expulsion of the last fraction with this particular example being that of reinjecting the red blood cells into the subject from whom they were removed at first instance.

Referring now to FIGS. 10, 11 and 12, there is shown an added component (plunger handle lock 90) which may be used with and which forms part of the present invention for the purpose of achieving a finer delineation between any two blood fractions.

Step 6a in FIG. 10 demonstrates the situation where the line of delineation D1 between any two blood fractions, as viewed in the delineation neck and as best seen in the expanded view of the transition point, is co-mingled or otherwise blended between the two adjoining blood fractions. The delineation may be considered as fuzzy. Plunger lock 90 has been placed to engage both the syringe barrel and the plunger handle such that that the piston assembly cannot move from it locked position during centrifuge operation.

As best seen in FIGS. 11 and 12, plunger lock 90 slips over barrel flange 18 and includes a set screw 92 threadable through flange 94 to engage a face 58 of handle 50 thereby locking the handle and the connected piston assembly in position.

Step 6b demonstrates the re-centrifuge of the blood sample shown in Step 6a with the piston assembly restrained in its locked position. As indicated by the expanded view in the illustration, re-centrifuging with the direction of centrifugal forces indicated by arrows may result in a significantly sharper line of delineation D2 between blood fractions.

Figure 13:
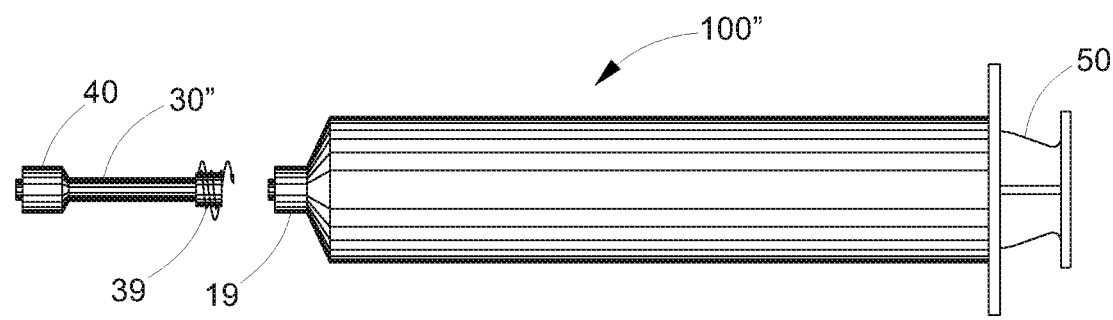
FIG. 13 is a side elevation view of a modified syringe barrel and a delineation neck releasably attachable to the modified barrel.

As is shown in various ones of the drawings, barrel 10 and delineation neck 30 of syringe 100 are integrally formed. However, this is not essential. By way of example, FIG. 13 illustrates a centrifugal syringe 100" wherein a delineation neck 30", now including an externally threaded coupler 39 at its proximal end, is releasably attachable to an internally threaded coupler 19 at the distal end of the syringe barrel.

Figure 15:
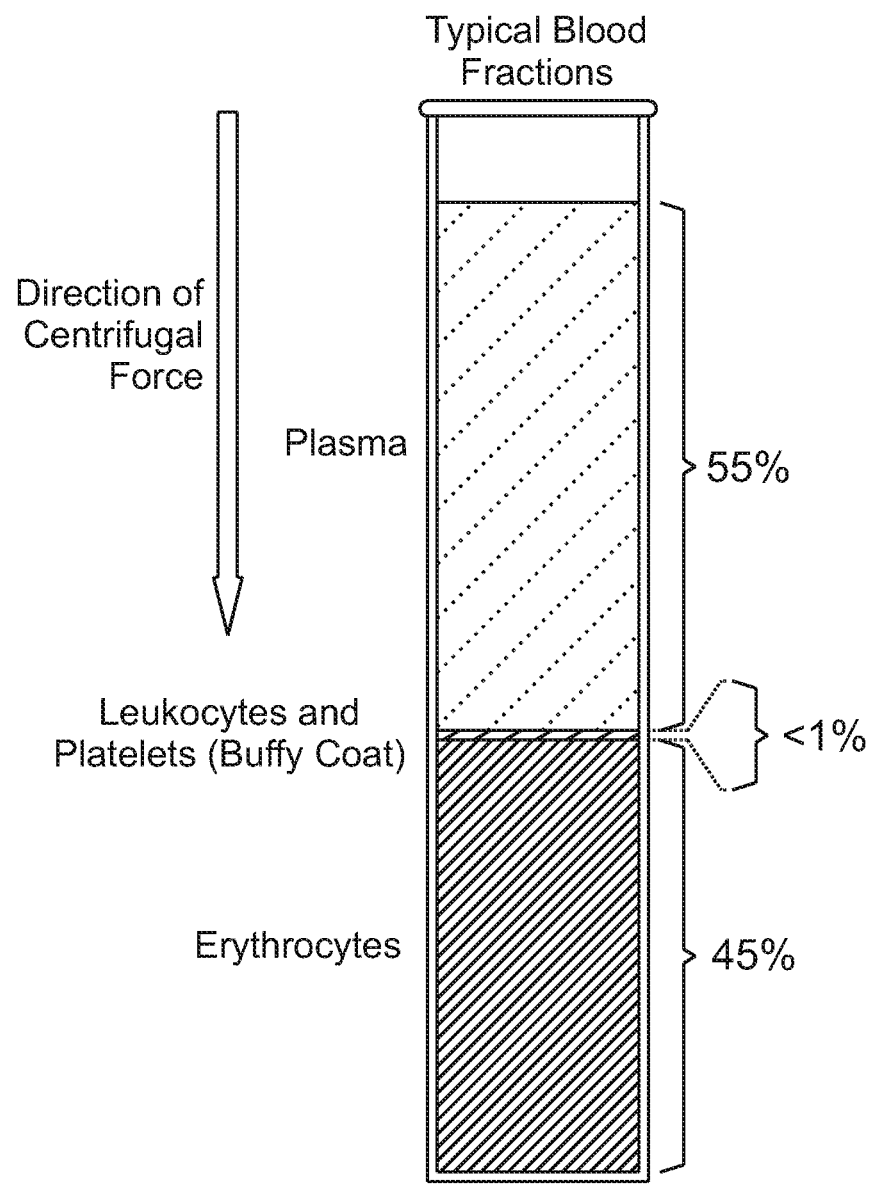
FIG. 15, as previously indicated, illustrates a column of blood together with an arrow indicating the direction of centrifugal force.

Referring now to FIG. 15, there is shown is a side view of a typical vile showing the, to-scale, fraction of erythrocytes at approximately 45%, platelets/leukocytes at less than 1% and plasma at approximately 55% of total blood volume. It is to demonstrate the complexity of attempting to isolate, or otherwise, segregate the very narrow band of platelets/leukocytes from the significantly higher volume of its adjacent erythrocytes and plasma without losing to or taking away from either of the two said adjacent blood components.

In operation, the present invention typically may be used as follows as illustrated by FIG. 9:

Step 1. A disposable syringe is removed from its sterile packaging with a hypodermic needle for the purpose of venipuncture, or otherwise the removal of blood from a patient by way of inserting the hypodermic needle into a vein and extracting blood. If needed, a blood anticoagulant may be added prior to venipuncture as a means of keeping the blood from clotting through potentially multiple centrifuging of the same sample.

Step 2. A full syringe of blood is extracted to the level of the piston assembly engages its stop mechanism within the barrel.

Step 3. Two sub-steps take place within Step 3. The needle is removed from the syringe and replaced with a sterile cap and the plunger handle is unthreaded, or otherwise removed from the piston assembly. The purpose of removing the plunger handle is to allow for reduced spin radius within a centrifuge.

Step 4. The full syringe is placed into a centrifuge carriage and pointed in either of two directions. The syringe chamber can be installed whereby the centrifugal force exerted on the blood, drives the densest material, that of red blood cells, towards the plunger piston assembly or the other way around towards the discharge/needle end of the syringe. The determining point as to which way the syringe is to be positioned into the centrifuge has to do with what blood fraction is to be expelled through the tip first. In the event that the red blood cells are needing to be expelled first, the syringe would be inserted with the capped needle-end facing away from the center of centrifuge rotation thus placing the most dense fractionation, red blood cells, at the needle end and consequently to be expelled first upon pushing the plunger into the barrel.

Step 5. Again, two sub-steps take place within Step 5. The plunger handle is reattached to the piston assembly to allow for the expelling of the blood fractions from the barrel. The blood can then be expelled into either a patient by attaching another hypodermic needle or other holding chamber, such as a blood bag, thus requiring the attachment of a sterile blood transport tube.

Step 6. The blood fractions are now expelled from the syringe using an inward force, most commonly thumb pressure, on the plunger handle. The point at which to stop expelling between blood fractionations has to do with expelling a particular fraction, (plasma first, as illustrated in Step 6 of FIG. 9) until such time as its delineation point between the two fractions enters the elongated neck whereby the much reduced cross sectional area of the neck allows for a much more specific dividing line between any two fractions. Once the plasma fraction has been expelled, and/or retained with the platelets, the much less volume of platelets can now be expelled until such time as the red blood cells show up in the elongated neck and a clear delineation can be seen between the two strata. In the event that an even finer line of delineation between either platelets and red blood cells or platelets and plasma needs to take place, the syringe can be centrifuged again so that a finer line between one fraction and the platelets can be seen in the transparent neck of the syringe. This optional auxiliary step, as illustrated in FIG. 10, requires a retainer or plunger lock to hold the piston assembly in place through the process of re-centrifuging.

Step 7. As illustrated in Steps 6 and 7 of FIG. 9, with the option of the red blood cells being centrifuged to the piston end of the syringe, and thus last to be expelled, a change of the attachment to the adapter at the end of the delineation neck may or may not need to take place at this point depending on the ultimate location of such cells. If the remaining blood, red cells, is needing to be re-injected into a patient, then another sterile needle would need to be attached and those cells re-introduced into the recipient from which they may or may not have originated.

As a concluding step, the syringe, needles and applicable hose will be disposed of under standard medical practice and protocol.

The scope of the claims should not be limited by the specific embodiments illustrated in the drawings, but should be given the broadest interpretation consistent with the description as a whole.

I claim:

1. A centrifugable syringe for use in blood fractionation, said syringe comprising:
    (a) a substantially transparent barrel having an axial bore defined by a bore wall, said bore extending from a mouth opening at a proximal end of said barrel to a distal end opening at a distal end of said barrel, each of said openings having an associated opening area, the opening area of said distal end opening being substantially less than the opening area of said mouth opening;
    (b) a substantially transparent, elongated delineation neck extending from a proximal end of said neck to a distal end of said neck,
        (i) said proximal end of said neck merging with said distal end of said barrel;
        (ii) said neck having an axial bore in fluid flow communication with the axial bore of said barrel; and,
        (iii) said axial bore of said neck extending lengthwise through said neck to an inlet/outlet opening in said neck at said distal end of said neck and having an opening area substantially the same as said opening area of said distal end opening of said barrel;
    (c) a syringe plunger; and,
    (d) a luer fitting at said distal end of said neck.

2. A syringe as defined in claim 1, wherein said plunger comprises:
    (a) a plunger piston assembly comprising:
        (i) a framework; and,
        (ii) a seal slidably bearing against said bore wall, said seal being supported by said framework within said bore; and,
    (b) a plunger handle releasably connected to said framework.

3. A syringe as defined in claim 2, wherein said seal comprises a flexible side wall slidably bearing against said bore wall and a flexible conical face projecting from said side wall forward of said framework, said conical face translating an axial force applied to said face to a lateral outward force on said side wall.

4. A syringe as defined in claim 2, said piston assembly further comprising a plurality of flexible locking tabs peripherally supported by said framework, said tabs flexing outwardly from said framework against said bore wall when said piston assembly is positioned in said bore away from said mouth opening and flexing further outwardly into a locking groove in said bore wall when said piston assembly is positioned in said bore at said mouth opening, egress of said piston assembly from said bore being restrained by said groove when said tabs are flexed into said groove.

5. A syringe as defined in claim 1, wherein said delineation neck is integrally formed with said barrel.

6. A syringe as defined in claim 1, wherein said proximal end of said delineation neck is releasably attachable to said distal end of said barrel.

7. A method of blood fractionation, comprising:
    (a) providing a syringe as defined in claim 1;
    (b) releasably connecting a needle device to said delineation neck;

(c) drawing blood from a subject through said needle device and said delineation neck into said syringe;
(d) disconnecting said needle device from said delineation neck;
(e) capping and sealing said inlet/outlet opening in said delineation neck with a removable capping device;
(f) centrifuging said blood within said syringe to separate the blood into delineable blood fractions;
(g) removing said capping device;
(h) expelling a delineated blood fraction through said inlet/outlet opening from said syringe.

8. A method as defined in claim 7, further including the step of recentrifuging at least a portion of said blood before all of said blood is expelled through said inlet/outlet to sharpen the delineation between any two blood fractions.

\* \* \* \* \*